(12) United States Patent
Taylor

(10) Patent No.: US 7,679,752 B2
(45) Date of Patent: Mar. 16, 2010

(54) METHODS FOR DETECTING PITCH IN LUMBER

(75) Inventor: Thomas J. Taylor, Seattle, WA (US)

(73) Assignee: Weyerhaeuser NR Company, Federal Way, WA (US)

( * ) Notice: Subject to any disclaimer, the term of this patent is extended or adjusted under 35 U.S.C. 154(b) by 506 days.

(21) Appl. No.: 11/535,791

(22) Filed: Sep. 27, 2006

(65) Prior Publication Data
US 2008/0074653 A1 Mar. 27, 2008

(51) Int. Cl.
G01N 21/47 (2006.01)
G01N 21/88 (2006.01)

(52) U.S. Cl. .................................. 356/446; 356/237.1

(58) Field of Classification Search ... 356/237.1–237.5, 356/445–446; 250/559.4, 559.45, 559.46; 702/33, 35, 36, 40
See application file for complete search history.

(56) References Cited

U.S. PATENT DOCUMENTS

| 4,149,089 | A | * | 4/1979 | Idelsohn et al. | 250/559.42 |
|---|---|---|---|---|---|
| 4,207,472 | A | * | 6/1980 | Idelsohn et al. | 250/559.46 |
| 4,221,974 | A | * | 9/1980 | Mueller et al. | 250/559.48 |
| 7,149,633 | B2 | * | 12/2006 | Woods et al. | 702/40 |
| 7,200,458 | B2 | * | 4/2007 | Carman et al. | 700/117 |
| 7,286,956 | B2 | * | 10/2007 | Floyd et al. | 702/159 |
| 7,304,740 | B1 | * | 12/2007 | Taylor | 356/405 |
| 7,324,904 | B2 | * | 1/2008 | Floyd et al. | 702/81 |
| 2005/0031158 | A1 | * | 2/2005 | Biernacki et al. | 382/100 |
| 2005/0040085 | A1 | * | 2/2005 | Carman et al. | 209/576 |
| 2005/0161118 | A1 | * | 7/2005 | Carman et al. | 144/403 |
| 2007/0119518 | A1 | * | 5/2007 | Carman et al. | 144/356 |
| 2007/0137323 | A1 | * | 6/2007 | Floyd et al. | 73/866 |
| 2007/0143066 | A1 | * | 6/2007 | Floyd et al. | 702/155 |
| 2007/0143075 | A1 | * | 6/2007 | Floyd et al. | 702/183 |
| 2008/0074653 | A1 | * | 3/2008 | Taylor | 356/237.1 |
| 2008/0074654 | A1 | * | 3/2008 | Taylor | 356/237.1 |

* cited by examiner

Primary Examiner—F. L Evans
(74) Attorney, Agent, or Firm—Rachael Vaughn

(57) ABSTRACT

Methods are provided for detecting compression wood, blue stain, or pitch in lumber. A light beam is projected towards the wood sample. Line or area cameras acquire images of light that is reflected from the wood sample. Based on the intensity of the reflected light at one or more locations on the wood sample, compression wood, blue stain, or pitch may be detected.

13 Claims, 7 Drawing Sheets

| RGB Color Image | Tracheid Effect Image (Laser line with line camera | Thresholded Tracheid Effect image showing Pitch areas |
|---|---|---|
| 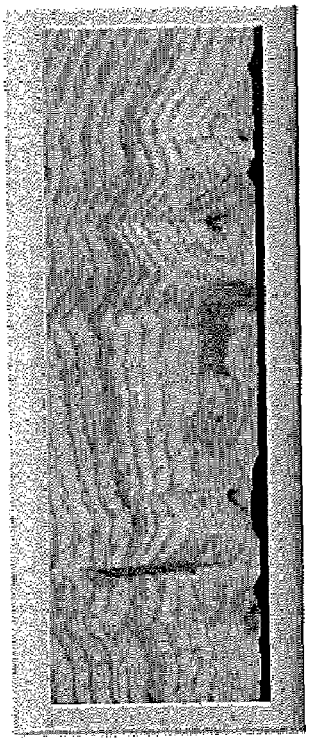 |  | 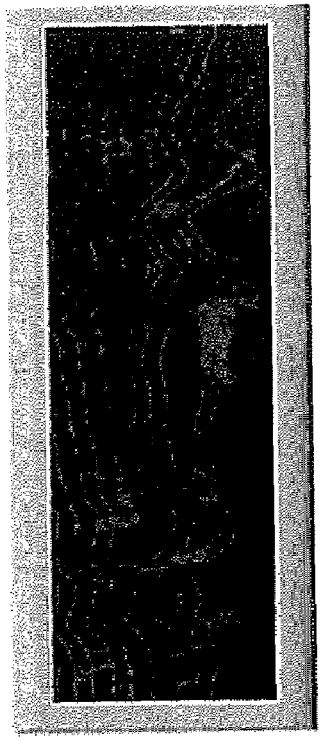 |
FIGURE 4

FIGURE 5
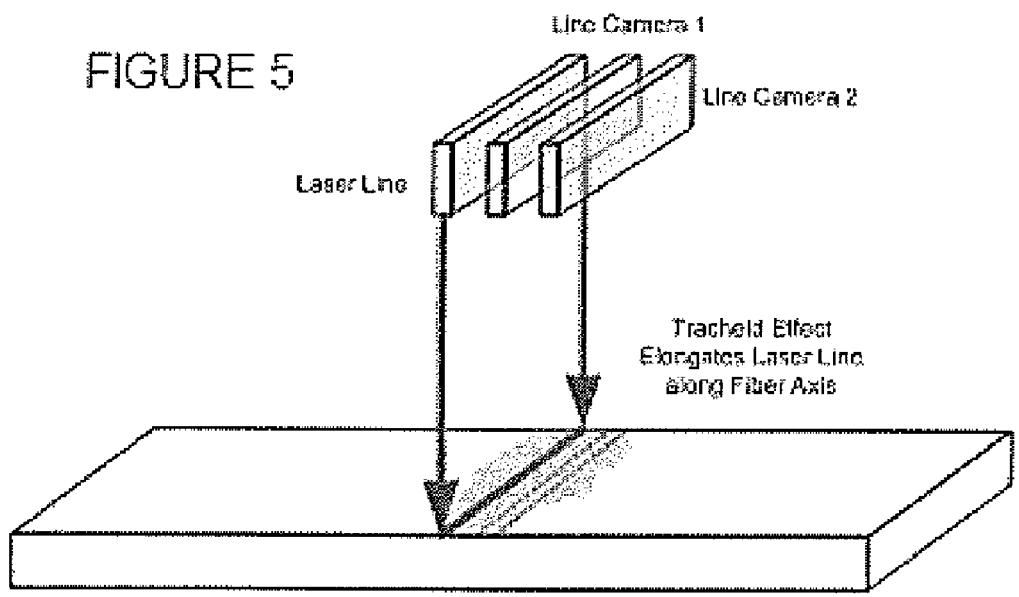
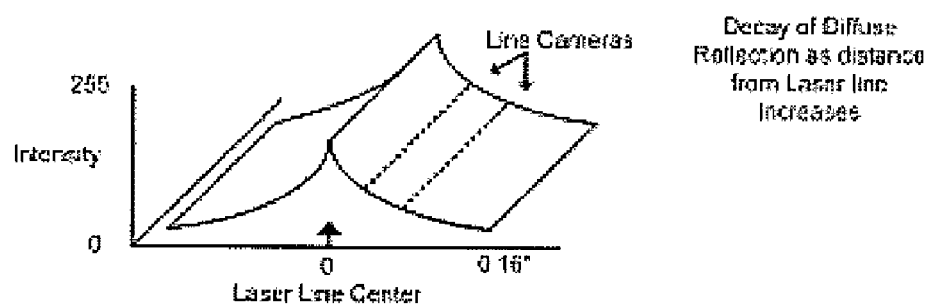

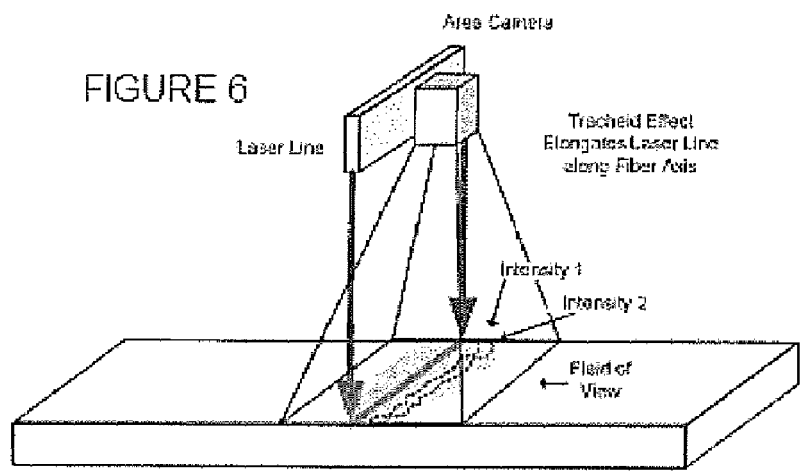
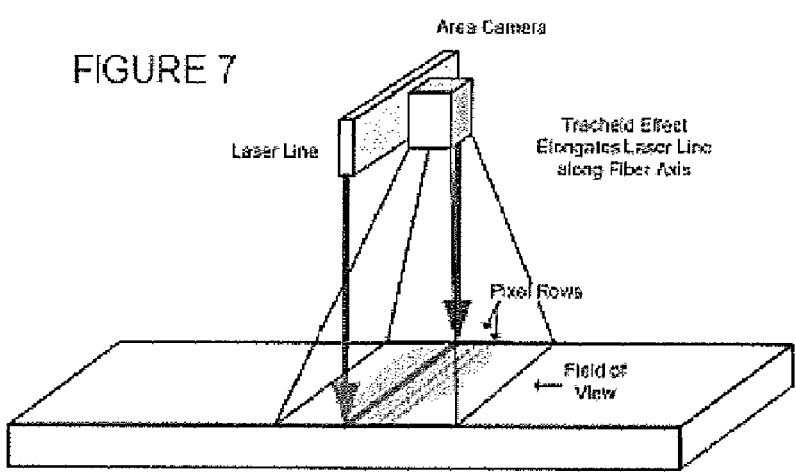

METHODS FOR DETECTING PITCH IN LUMBER

FIELD OF THE INVENTION

This invention relates generally to methods for detecting pitch in lumber.

BACKGROUND OF THE INVENTION

It is generally known to identify compression wood, blue stain, and pitch in a wood sample. With respect to detecting compression wood, known methods would include optical and scanning electron microscopy to identify compression wood areas. In normal wood, the S2 layer (the thickest cell wall layer comprised of ordered microfibrils nearly parallel to the long axis of the cell) is continuous and characterized by low microfibril angles. In compression wood the S2 layer is fractured and is characterized by high microfibril angles. Microscopy methods have the disadvantage that they cannot be applied in real time, in an industrial setting with lumber moving at planar speeds (up to 2500 fpm). The other primary method used to identify compression wood consists of transmission imaging of thin cross sections of boards. In this method, thin cross sections are imaged in transmission mode either in a scanner or photographic setup. Areas of compression wood appear as relatively opaque areas. The severity of compression wood can be estimated by mapping the variation in opacity in these areas. More severe compression wood transmits less light than less severe areas. The thin section transmission method, however, is also not appropriate for a real-time industrial application for obvious reasons. In addition, methods for detection of blue stain and pitch have demonstrated shortcomings.

Accordingly, a need exists for methods for more efficient detection of compression wood, blue stain, or pitch in lumber.

BRIEF DESCRIPTION OF THE DRAWINGS

The embodiments of the present invention are described in detail below with reference to the following drawings.

FIG. 4 is an illustration of the appearance of pitch, its effect on the tracheid effect, and it's detection by thresholding the tracheid image;

FIG. 5 is a diagram of a detection system implementing line cameras;

FIG. 6 is a diagram of a detection system implementing an area camera;

FIG. 7 is a diagram of a detection system implementing an area camera;

DETAILED DESCRIPTION OF THE INVENTION

The present invention generally relates to detection of compression wood, blue stain, or pitch in a wood sample. A light beam is projected towards the wood sample. The light beam may be in the form of a laser line. In an embodiment, the light beam may be in the form of individual spots of light. Line or area cameras acquire images of light that is reflected from the wood sample. Based on the intensity of the reflected light at one or more locations on the wood sample, compression wood, blue stain, or pitch may be detected.

Compression Wood Detection in Lumber

In an embodiment, the compression wood detection system is directed to transporting lumber longitudinally past an image acquisition system. The imaging system consists of laser lines projected across the width of the board faces (top and bottom) and either line cameras or area cameras to record the intensity of diffusely reflected light on either side of the laser line. The method can be extended to include the board edges as well with additional or modified hardware.

The laser line may be of sufficient intensity to saturate or nearly saturate the cameras at integration times which are of a duration allowing for minimal board movement during the integration period, such as, for example, less than 0.1 inch at 2000 feet per minute board speed. The laser wavelength may be red or near infra-red, such as for example, 680-850 nm.

The line camera imaging system consists of two or more line cameras (one set for each board face) where the lines are aimed parallel to and at fixed distances from the center of the laser line; one line camera being aimed closer to the laser line and the second being aimed further from the center. In this way, the two lines measure the intensity drop of the diffuse reflection of the laser, which is representative of the T1 or 'tracheid' effect, known by those skilled in the art.

If area cameras are being used, multiple laser lines can be projected in the field of view, and a single frame capture can be used to image a larger area of the board (e.g. full width and 12 inches along the length). In this case, laser lines should be spaced so that they are separated by dark areas.

Figure 1:
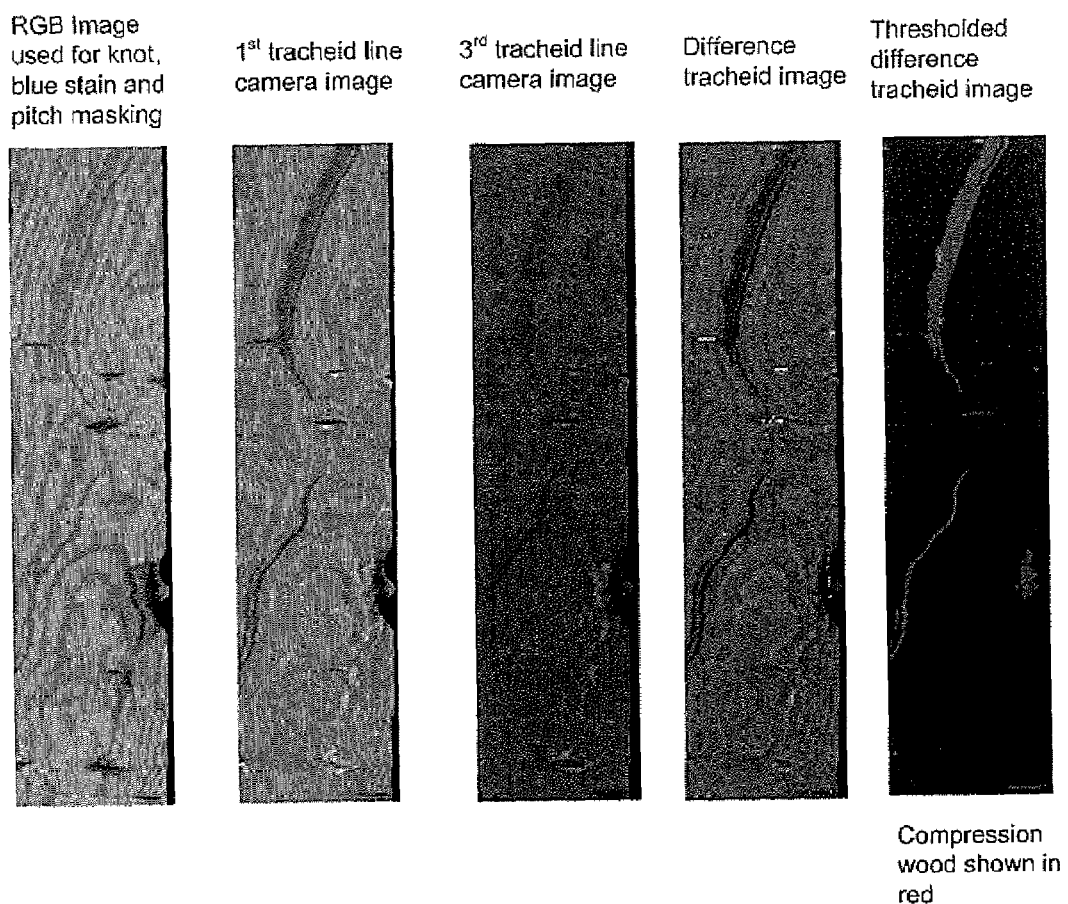
FIG. 1 is an illustration of compression wood detection steps.

In this way, the decay or fall off of the diffusely reflected laser light (T1 effect) can be measured on wood (illustrated in FIG. 1 for the line camera example).

Areas of compression wood contain cells with high microfibril angles in the S2 layer of the cell wall. The high microfibril angle of compression wood blocks the transmission of the laser light along the axis of the cell. In contrast, normal latewood contains cells with relatively lower microfibril angles in the S2 layer which transmits laser light more effectively. Therefore, the diffuse reflection intensity in compression wood areas decreases more rapidly than in areas of normal wood. As a result, the intensity along the first line camera (as in the example illustrated in FIG. 1) will be lower in compression wood than in normal latewood. Therefore, the difference in intensity between the first line and a more remote line will be lower in areas of compression wood compared with normal late wood. The intensity difference between the two line cameras (or pixel row if using an area camera) is representative of the slope of the decay in intensity and is a more robust measurement in compression wood identification than intensity alone. In a sense, using the slope or difference of intensity helps normalize the measurement for color differences in wood. In addition to the cameras, the imaging system may require processing software to perform image analysis steps.

For an embodiment in which a line camera is used, the method may have the steps of acquiring successive simultaneous images from the set of line cameras for the entire length of the board; reassembling consecutive scans to create an image of the board from each of the line cameras; using a 'perimeter' image (acquired from separate geometric scanning system) to 'straighten' the board to remove any effects of sniping through the scanner; using a 'wane perimeter' image (acquired from a separate geometric scanning system) to locate any wane areas and use this information to create a wane mask. Wane area affects the reflection intensity of the laser line and is not processed further. The use of a geometric scanning system assures that only those parts of the board surface which can be properly imaged are used in the detection of compression wood.

In additional steps, knots, blue stain and pitch are identified using color (RGB) images (acquired from separate color scanning system) and these areas are masked from processing for compression wood. Knots and blue stain attenuate the diffuse reflection of the laser line and interfere with a compression wood algorithm. Pitch intensifies the diffuse reflection of the laser line and also interferes with the compression wood algorithm.

In further steps, the more remote tracheid image (that furthest from the center of the laser line) is subtracted from the nearest tracheid image (that closest to the center of the laser line), to create a 'difference' image. Note that areas masked for wane, knots, blue stain and compression wood should not be processed or should be represented by zero intensity.

Next, the 'difference' image is thresholded between two grey scale intensities. The lower and upper threshold limits will be dependent on the camera and laser setup and may need to be adjusted for each system. The upper and lower threshold limits are set by manually identifying compression wood areas on imaged boards either by wood scientists or by thin section transmission measurements. Thresholds are then set so that the image area between the upper and lower thresholds match that of the manually identified compression wood. Following thresholding, small 'particles' of compression wood are removed from the thresholded difference image. Small 'holes' in compression wood areas are filled in from the thresholded difference image.

Figure 2:
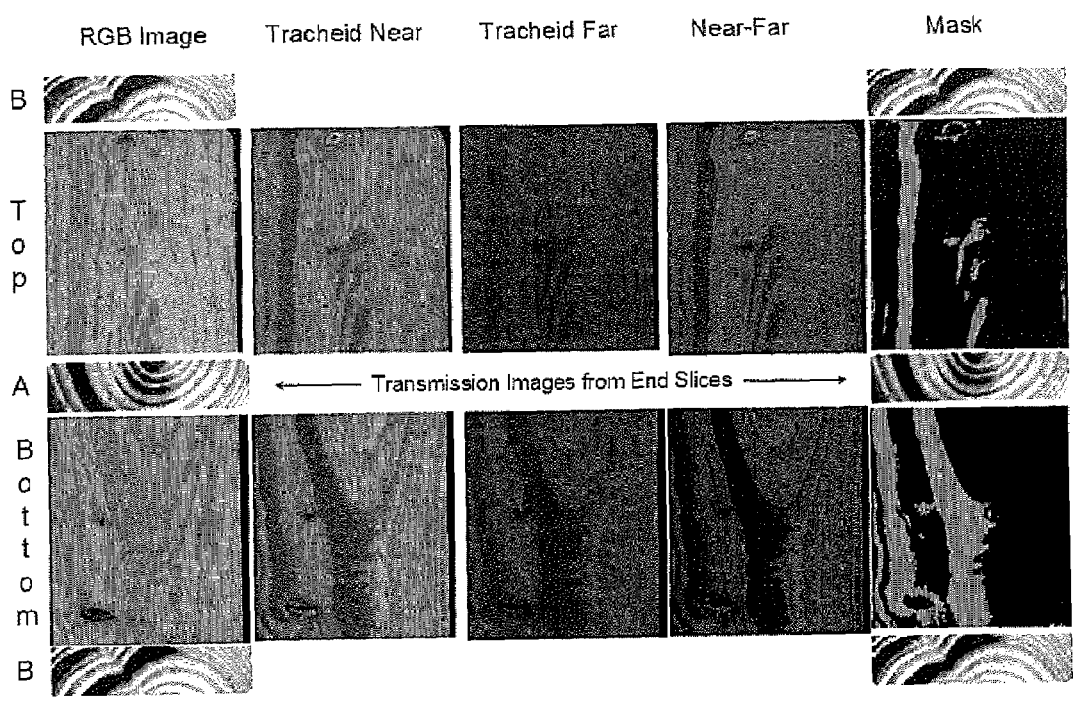
FIG. 2 is an illustration of the correlation of this compression wood method with the method using light transmission in thin slices.

A visual example of the technique is shown in FIG. 2. For this example, the lower intensity threshold was set at 12 grey scale value (0-255); the upper intensity threshold was set at 35 grey scale value.

In addition to the method steps mentioned above, the method could also include several modifications. These would include using additional color information to limit the amount of area identified as compression wood. As is evident in the example described above and illustrated in FIG. 2, compression wood areas tend to appear as wider areas of latewood in a tracheid effect image, compared to that in normal wood. By using a color mask in addition to the thresholded difference image, a more robust measure of compression wood may be possible. One way to make a color mask for compression wood application would be to convert RGB images to HSI space (hue, saturation, intensity) and to limit compression wood areas to those containing certain hues (primarily), and intensities. This variation in the method will probably need to be adjusted for each species and perhaps even geographies.

There is good correlation between the thin-section transmission method and the identification of compression wood by the intensity difference method outlined above. Shown in FIG. 2 is an example of this correlation. Top and bottom faces from RGB and laser line cameras are shown together with transmission light images from corresponding slices from the end of the same board section. Notice that the method described here accurately identifies the location of compression wood bands obvious in the transmission images of the end slices.

In an embodiment, a method is provided for detecting compression wood in a wood sample. A system for practicing the method is illustrated in FIG. 5. The method has the steps of: projecting a coherent light beam toward a first section of the wood sample; acquiring a first image of reflected light using a first line camera; measuring a first intensity of the reflected light based on the first image; acquiring a second image of reflected light using a second line camera; measuring a second intensity of the reflected light based on the second image; measuring a difference between the first intensity and the second intensity; and detecting an area of compression wood in the wood sample wherein the detection is based on whether the difference between the first intensity and the second intensity is within a predetermined intensity range.

In another embodiment, a method is provided for detecting compression wood in a wood sample. A system for practicing the method is illustrated in FIG. 7. The method has the steps of: projecting one or more coherent light beams toward a first section of the wood sample; acquiring an image of the first section using an area camera; measuring a first intensity of reflected light along a first pixel row based on the image; measuring a second intensity of reflected light along a second pixel row based on the image; measuring a difference between the first intensity and the second intensity; and detecting an area of compression wood in the wood sample wherein the detection is based on whether the difference between the first intensity and the second intensity is within a predetermined intensity range.

In another embodiment, a method is provided for detecting compression wood in a wood sample. A system for practicing the method is illustrated in FIG. 6. The method has the steps of: projecting one or more coherent light beams toward a first section of the wood sample; acquiring an image of the first section using an area camera; predetermining a first intensity; determining a first distance from the light beam at which a measured reflected intensity is equal to the predetermined first intensity; predetermining a second intensity; determining a second distance from the light beam at which a measured reflected intensity is equal to the predetermined second intensity; measuring a difference between the first distance and the second distance; and detecting an area of compression wood in the wood sample wherein the detection is based on whether the difference between the first distance and the second distance is within a predetermined distance range.

Blue Stain Detection in Lumber

The blue stain detection system consists of a method for transporting lumber longitudinally past an image acquisition system. The imaging system consists of a full spectrum light source and either an area RGB camera per face, such as that illustrated in FIG. 8, or three line cameras per face (one each for red, green, and blue), such as that illustrated in FIG. 9. The method can be extended to include the board edges as well with additional or modified hardware.

The full spectrum light source should be of sufficient intensity to saturate or nearly saturate the cameras at integration times which are of a duration allowing for minimal board movement during the integration period (<0.1" at 2000 fpm board speed). In addition to the cameras, the imaging system may require processing software to perform image analysis steps.

For an embodiment in which line cameras are used, the method may have the steps of acquiring successive simultaneous images from each of the line cameras for the entire board; reassembling consecutive scans to create an image of the board from each of the line cameras (red, green and blue channels); using a 'perimeter' image (acquired from separate geometric scanning system) to 'straighten' the board to remove any effects of sniping through the scanner; using a 'wane perimeter' image (acquired from separate geometric scanning system) to locate any wane areas and use this to create a wane mask. Wane area affects the reflection intensity of the laser line and is not processed further.

In an additional step, the individual color channels are low pass filtered. This will prevent creation of color artifacts created by combining data from cameras which are not perfectly registered. Various filter types can be used, such as, for example, a 3×3 convolution filter. Note that this step may not be required for systems using area cameras.

The data is then combined from all three colors and converted to HSI (Hue, Saturation, Intensity) color space. In a next step, each HSI channel is thresholded at two levels. In an alternate embodiment, only the hue channel can be thresholded. The thresholded HSI images are combined to produce the blue stain image. In some cases, it may be useful to further filter the blue stain image map with, for example, a 3×3 automedian filter. The thresholds are for hue (and, subsequently saturation and intensity) are set by manually identifying blue stain areas on one or many boards, and adjusting the upper and lower hue threshold such that only those areas manually identified on the board are maintained in the image.

Figure 3:
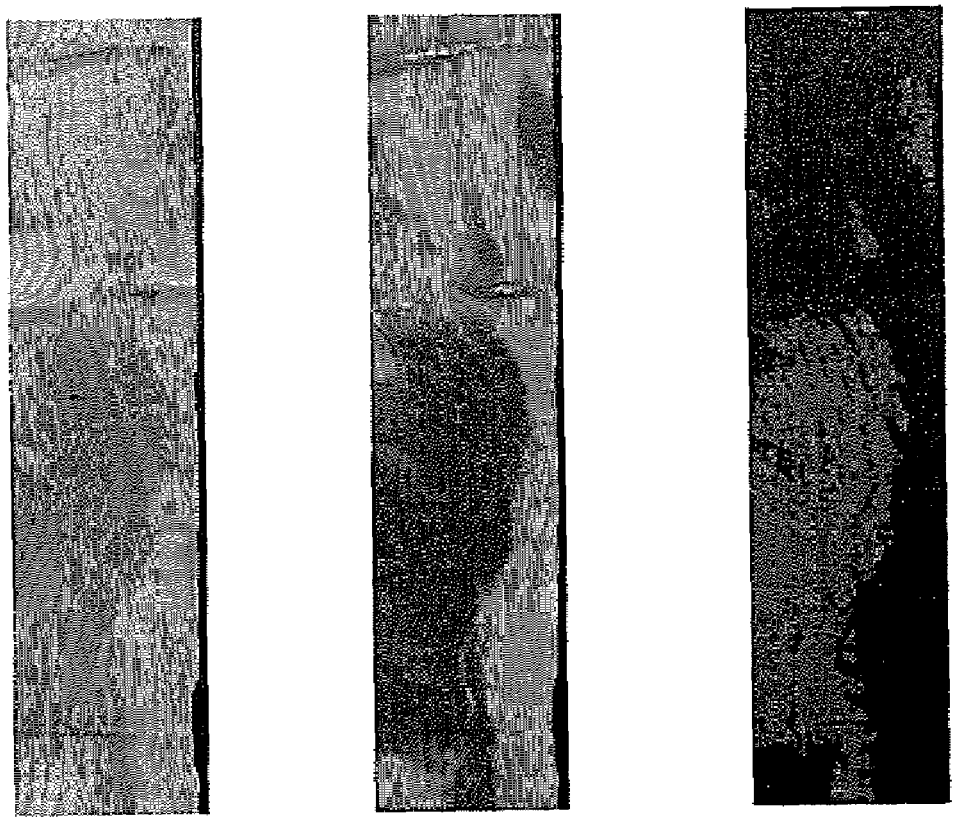
FIG. 3 is an illustration of blue stain on southern pine, its effect on the tracheid image and detection using the HSI method.

A visual example of this technique is shown in FIG. 3. For this example, the hue threshold limits were 34-106; the saturation threshold limits were 2-60 and the intensity threshold limits were 2-106.

Figure 9:
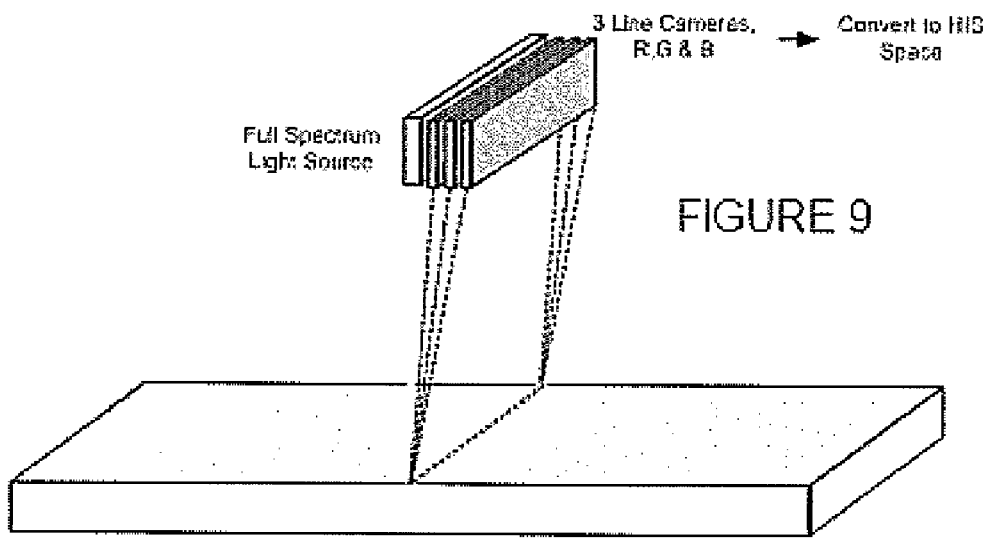
FIG. 9 is a diagram of a detection system implementing multiple line RGB cameras.

In an embodiment, a method is provided for detecting blue stain in a wood sample. A system for practicing the method is illustrated in FIG. 9. The method has the steps of: projecting a full spectrum light beam toward a first section of the wood sample; acquiring a first image of reflected light using a first line camera; measuring an intensity of reflected light in a red region of the full spectrum based on the first image; acquiring a second image of reflected light using a second line camera; measuring an intensity of reflected light in a green region of the full spectrum based on the second image; acquiring a third image of reflected light using a third line camera; measuring an intensity of reflected tight in a blue region of the full spectrum based on the third image; subjecting the intensity measurements of reflected light in the red, green and blue regions to an algorithm to provide hue, saturation and intensity data; and detecting blue stain in the wood sample based on whether the hue data is within a pre-selected hue range.

Figure 8:
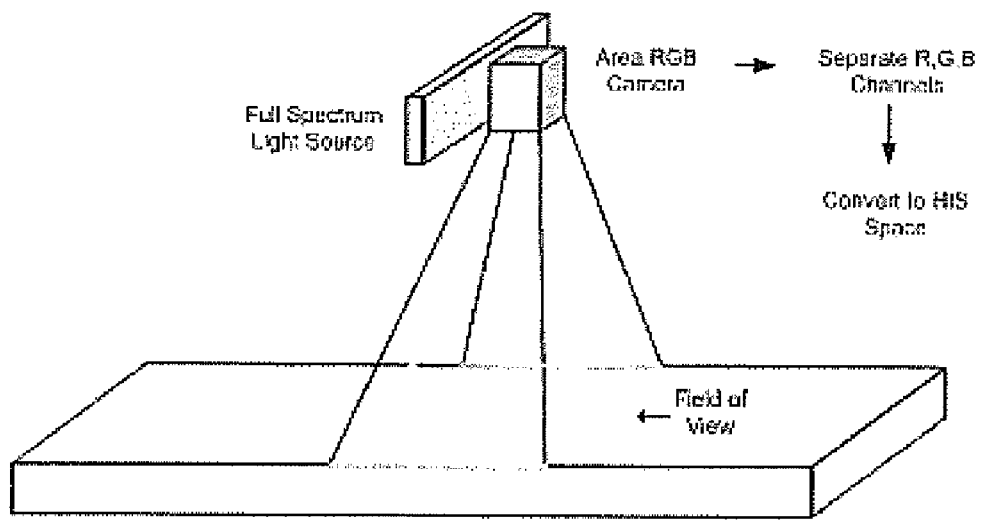
FIG. 8 is a diagram of a detection system implementing an area RGB camera.

In an embodiment, a method is provided for detecting blue stain in a wood sample. A system for practicing the method is illustrated in FIG. 8. The method has the steps of: projecting a full spectrum light beam toward a first section of the wood sample; acquiring a first image of reflected light using an area camera; measuring an intensity of reflected light in a red region of the full spectrum based on the first image; measuring an intensity of reflected light in a green region of the full spectrum based on the first image; measuring an intensity of reflected light in a blue region of the full spectrum based on the first image; subjecting the intensity measurements of reflected light in the red, green and blue regions to an algorithm to provide hue, saturation and intensity data; and detecting blue stain in the wood sample based on whether the hue data is within a pie-selected hue range.

There are several descriptions of blue stain detection in wood in the prior art. Most involve area cameras and some thresholding in RGB color space. The method outlined here may be more beneficial in several ways. First, it involves a processing step to allow the use of line cameras for color information from separate channels in order to reduce the introduction of color artifacts created by slight mis-registrations of those cameras. The convolution filter used averages the color information across several pixels with appropriate weighting and virtually eliminates color artifacts.

Secondly, the method is unique in that it converts the color information from RGB space to HSI space. While blue stain detection is possible in the RGB color space, conversion to HSI space allows the hue channel to be used as the primary detection channel since the blue stain hue is fairly consistent and different from normal unstained wood. It is easier to set the threshold levels with the single hue channel than trying to set all three RGB channels. After hue range is selected, the saturation and intensity channels can be used to refine the mask. Interestingly, using the blue channel of an RGB image is not an effective way to detect blue stain; all three colors may need to be utilized.

Finally, the application of a blue stain mask to image processing of tracheid effect information is not taught in the prior art. As shown in FIG. 3, blue stain dramatically affects the diffuse reflection intensity used to measure the tracheid effect and may interfere with, among others, the detection of compression wood.

Pitch Detection in Lumber

Pitch in wood has the effect of transmitting laser light to a greater extent along the fiber axis than normal wood (the tracheid effect) and may interfere with detection of wood features which rely on the tracheid effect (e.g., compression wood). Identification of pitch in wood relies on a system which measures the intensity of diffusely reflected laser light at a distance from a laser light source using line cameras or area cameras, such as the systems illustrated in FIGS. 5, 6 and 7. Pitch is identified in areas where the intensity exceeds an intensity threshold at a certain distance from the laser line (line camera location or area camera pixel row). The intensity threshold is system dependent and is affected by the laser intensity, distance between the laser line center and the line camera focus, integration time of the camera and overall reflectivity of the wood. The intensity threshold may be set by manually identifying areas of pitch and adjusting the threshold until the area exceeding the threshold intensity matches the manually identified areas of pitch.

Alternately, using area cameras, pitch could be detected as areas where the intensity persists above a certain level for greater than a given distance from the laser light.

In an embodiment, the pitch detection system consists of a method for transporting lumber longitudinally past an image acquisition system. The imaging system consists of laser line(s) projected across the width of the board faces (top and bottom) and either line cameras or area cameras to record the intensity of diffusely reflected light from the laser line(s). The method can be extended to include the board edges as well with additional or modified hardware.

The laser line(s) should be of sufficient intensity to saturate or nearly saturate the cameras (e.g. ~255 grey scale level for an 8-bit camera) at integration times which are of a duration allowing for minimal board movement during the integration period (<0.1" at 2000 fpm board speed). The laser wavelength may be red or near infra-red (680-850 nm).

The line camera imaging system consists of a line camera aimed parallel to and at a fixed distance from the center of the laser line. In this way, the line measures the intensity and intensity drop of the diffuse reflection of the laser, which is representative of the T1 or 'tracheid' effect. Areas where the line camera records an intensity above a threshold value are identified as pitch containing wood.

If area cameras are being used, one or multiple laser lines can be projected in the field of view, and a single frame capture can be used to image a larger area of the board (e.g. full width and 12" along the length). In this case, laser lines should be spaced so that they are separated by dark areas. If the area camera field of view is precisely aligned to the laser line, the reflected intensity can be measured at various distances from the center of a laser line by selecting individual pixel rows. Areas exceeding the intensity threshold are identified as pitch.

Alternately, an intensity value can be selected and the distance from the center of the laser line to the point where the diffusely reflected intensity drops below this level can be measured. In this case, a distance threshold can be set to identify pitch. Areas where the distance from the laser line to the point where the intensity drops below a chosen value exceeds a threshold distance are identified as pitch.

In addition to the cameras, the imaging system requires processing software to perform image analysis steps. Such software is known by those skilled in the art. In an embodiment, the method has the steps of: acquiring images from line cameras for the entire board; reassembling consecutive scans to create an image of the board from each of the line cameras; using a 'perimeter' image (acquired from a separate geometric scanning system) to 'straighten' the board to remove any effects of sniping through the scanner.

Use of a 'wane perimeter' image (acquired from a separate geometric scanning system) enables location of wane areas and in order to create a wane mask. Wane area affects the reflection intensity of the laser line and may not be not processed further. The tracheid effect image is then thresholded using a single threshold level. The threshold limit will be dependent on the camera and laser setup and needs to be adjusted for each system. Small 'holes' in pitch containing areas are filled in to create a more continuous mask.

A visual example of the technique is shown in FIG. 4. For this example, the pitch threshold was set at 180 grey scale level (on a scale of 0-255).

In a n embodiment, a method is provided for detecting pitch in a wood sample. The method has the steps of: projecting a coherent light beam toward a first section of the wood sample; acquiring a first image of reflected light using a first line camera focused at a predetermined distance from the center of the light beam; measuring a first intensity of the reflected light based on the first image; and detecting pitch within the wood sample based on whether the first intensity is greater than a threshold intensity.

In another embodiment, a method is provided for detecting pitch in a wood sample. The method has the steps of: projecting one or more coherent light beams toward a first section of the wood sample; acquiring an image of the first section using an area camera; measuring a first intensity of reflected light along a first pixel row based on the image wherein the first pixel row is based on a predetermined distance from the light beam; and detecting pitch within the wood sample based on whether the first intensity is greater than a threshold intensity.

In another embodiment, a method is provided for detecting pitch in a wood sample. The method has the steps of: projecting one or more coherent light beams toward a first section of the wood sample; acquiring an image of the first section using an area camera; predetermining a first intensity; determining a first distance from the light beam at which an intensity of reflected light is equal to the predetermined first intensity; and detecting pitch within the wood sample based on whether the first distance is greater than a threshold distance.

The present invention has advantages over the prior art in that a tracheid effect image system can be used to identify pitch pockets. Most pitch detection systems which rely on imaging systems use RGB color images for identification of pitch areas. The appearance of pitch in a tracheid effect (diffuse reflected laser light) image is a dramatic and reliable method. The image processing required for pitch detection from a tracheid effect image is a simple, one level thresholding and is, therefore, accomplished in real time. In addition, the use of a pitch mask to exclude areas in other defect detection methods (e.g. compression wood) may prove beneficial.

While the embodiments of the invention have been illustrated and described, as noted above, many changes can be made without departing from the spirit and scope of e invention. Accordingly, the scope of the invention is not limited by the disclosure of the embodiments. Instead, the invention should be determined entirely by reference to the claims that follow.

What is claimed is:

1. A method for detecting pitch in a wood sample, the method comprising the steps of:
   projecting a coherent light beam toward a first section of the wood sample;
   acquiring a first image of reflected light using a first line camera focused at a predetermined distance from a center of the light beam;
   measuring a first intensity of the reflected light based on the first image; and
   detecting pitch within the wood sample based on whether the first intensity is greater than a threshold intensity.

2. The method of claim 1 wherein the coherent light beam is a laser.

3. The method of claim 1 wherein the light beam creates a line of light across the first section.

4. The method of claim 3 wherein the line of light is in the form of individual spots of light.

5. A method for detecting pitch in a wood sample, the method comprising the steps of:
   projecting one or more coherent light beams toward a first section of the wood sample;
   acquiring an image of the first section using an area camera;
   measuring first intensity of reflected light along a first pixel row based on the image wherein the first pixel row is based on a predetermined distance from the light beam; and
   detecting pitch within the wood sample based on whether the first intensity is greater than a threshold intensity.

6. The method of claim 5 wherein the coherent light beam is a laser.

7. The method of claim 5, wherein at least one of the one or more coherent light beams has a wavelength in a range from 680 nm to 850 nm.

8. A method for detecting pitch in a wood sample, the method comprising the steps of:
   projecting one or more coherent light beams toward a first section of the wood sample;
   acquiring an image of the first section using an area camera;
   predetermining a first intensity;
   determining s first distance from the light beam a which an intensity of reflected light is equal to the predetermined first intensity; and detecting pitch within the wood sample based on whether the first distance is greater than a threshold distance.

9. The method of claim 8 wherein the light beam is a laser.

10. The method of claim 8 wherein the light beam creates a line of light across the first section.

11. The method of claim 8 wherein the line of light is in the form of individual spots of light.

12. The method of claim 8, wherein at least one of the one or more coherent light beams has a wavelength in a range from 680 nm to 850 nm.

13. A method for detecting pitch in a wood sample the method comprising the steps of:

projecting a coherent light beam toward a first section of the wood sample, wherein the light beam has a wavelength in a range from 680 nm to 850 nm;

acquiring a first image of reflected light using a first line camera focused at a predetermined distance from a center of the light beam;

measuring a first intensity of the reflected light based on the first image; and detecting pitch within the wood sample based on whether the first intensity is greater than a threshold intensity.

* * * * *

UNITED STATES PATENT AND TRADEMARK OFFICE
CERTIFICATE OF CORRECTION

| | | |
|---|---|---|
| PATENT NO. | : 7,679,752 B2 | Page 1 of 1 |
| APPLICATION NO. | : 11/535791 | |
| DATED | : March 16, 2010 | |
| INVENTOR(S) | : Thomas J. Taylor | |

It is certified that error appears in the above-identified patent and that said Letters Patent is hereby corrected as shown below:

Col. 8, Line 47, should read as follows:

... measuring a first intensity of reflected light along a first pixel ...

The word "a" between measuring and first was omitted.

Col. 8, Line 65, should read as follows:

... determining a first distance from the light beam at which an ...

The letter "s" following the word determining should be an "a", and the letter "a" following the word beam should be the word "at".

Signed and Sealed this

Fourth Day of May, 2010

David J. Kappos
*Director of the United States Patent and Trademark Office*